United States Patent
Romesburg

(10) Patent No.: US 11,350,884 B2
(45) Date of Patent: Jun. 7, 2022

(54) PHYSIOLOGICAL METRIC ESTIMATION RISE AND FALL LIMITING

(71) Applicant: Valencell Inc., Raleigh, NC (US)

(72) Inventor: Eric Douglas Romesburg, Chapel Hill, NC (US)

(73) Assignee: Valencell, Inc., Raleigh, NC (US)

( * ) Notice: Subject to any disclaimer, the term of this patent is extended or adjusted under 35 U.S.C. 154(b) by 559 days.

(21) Appl. No.: 15/661,220

(22) Filed: Jul. 27, 2017

(65) Prior Publication Data

US 2017/0332974 A1 Nov. 23, 2017

Related U.S. Application Data

(63) Continuation of application No. 14/370,658, filed as application No. PCT/US2012/071593 on Dec. 24, 2012, now Pat. No. 10,390,762.

(60) Provisional application No. 61/586,874, filed on Jan. 16, 2012.

(51) Int. Cl.
  *A61B 5/00* (2006.01)
  *A61B 5/024* (2006.01)
  *A61B 5/1455* (2006.01)

(52) U.S. Cl.
  CPC ........ *A61B 5/7235* (2013.01); *A61B 5/02416* (2013.01); *A61B 5/14551* (2013.01); *A61B 5/6801* (2013.01); *A61B 5/7203* (2013.01); *A61B 5/742* (2013.01); *A61B 5/02438* (2013.01); *A61B 5/6815* (2013.01);
  (Continued)

(58) Field of Classification Search
  CPC ... A61B 5/7235; A61B 5/7203; A61B 5/6801; A61B 5/742; A61B 5/14551; A61B 5/02416; A61B 5/7257; A61B 2560/0223; A61B 5/02438; A61B 5/6815; A61B 5/725
  See application file for complete search history.

(56) References Cited

U.S. PATENT DOCUMENTS

| | | | |
|---|---|---|---|
| 3,636,617 A | 1/1972 | Schmidt et al. |
| 3,704,706 A | 12/1972 | Herczfeld et al. |
| 4,672,976 A | 6/1987 | Kroll |

(Continued)

FOREIGN PATENT DOCUMENTS

| | | | |
|---|---|---|---|
| CN | 1545979 A | 11/2004 |
| CN | 101317188 A | 12/2008 |

(Continued)

OTHER PUBLICATIONS

Coote 2009 Exp. Physiol. 95.3:431-440 (Year: 2009).*

(Continued)

*Primary Examiner* — Colin T. Sakamoto
*Assistant Examiner* — Patrick M Mehl
(74) *Attorney, Agent, or Firm* — Coats + Bennett, PLLC

(57) ABSTRACT

Methods and apparatus disclosed herein use a filtering technique to improve the accuracy of the results achieved when processing data provided by a physiological sensor. The disclosed filtering technique corrects many of the accuracy problems associated with physiological sensors, particularly PPG sensors. Broadly, the filtering technique adjusts a current filtered estimate of a physiological metric as a function of a rate limit based on a comparison between an instantaneous estimate of the physiological metric and the current filtered estimate.

38 Claims, 6 Drawing Sheets

(52) U.S. Cl.
CPC ............ *A61B 5/725* (2013.01); *A61B 5/7257* (2013.01); *A61B 2560/0223* (2013.01)

(56) References Cited

U.S. PATENT DOCUMENTS

| | | | |
|---|---|---|---|
| 4,952,928 A | 8/1990 | Carroll et al. | |
| 4,955,379 A | 9/1990 | Hall | |
| 5,139,025 A | 8/1992 | Lewis et al. | |
| 5,243,992 A | 9/1993 | Eckerle et al. | |
| 5,297,548 A | 3/1994 | Pologe | |
| 5,299,570 A | 4/1994 | Hatschek | |
| 5,448,082 A | 9/1995 | Kim | |
| 5,482,036 A | 1/1996 | Diab et al. | |
| 5,494,043 A | 2/1996 | O'Sullivan et al. | |
| 5,503,016 A | 3/1996 | Koen | |
| 5,575,284 A | 11/1996 | Athan et al. | |
| 5,673,692 A | 10/1997 | Schulze et al. | |
| 5,807,267 A | 11/1998 | Bryars et al. | |
| 5,846,190 A | 12/1998 | Woehrle | |
| 5,853,005 A | 12/1998 | Scanlon | |
| 5,906,582 A | 5/1999 | Kondo et al. | |
| 5,908,396 A | 6/1999 | Hayakawa et al. | |
| 5,941,837 A | 8/1999 | Amano et al. | |
| 5,954,644 A | 9/1999 | Dettling et al. | |
| 5,964,701 A | 10/1999 | Asada et al. | |
| 6,022,748 A | 2/2000 | Charych et al. | |
| 6,042,549 A | 3/2000 | Amano et al. | |
| 6,067,462 A * | 5/2000 | Diab ................ | A61B 5/02416 600/310 |
| 6,198,394 B1 | 3/2001 | Jacobsen et al. | |
| 6,241,684 B1 | 6/2001 | Amano et al. | |
| 6,267,721 B1 | 7/2001 | Welles | |
| 6,393,311 B1 | 5/2002 | Edgar, Jr. et al. | |
| 6,443,890 B1 | 9/2002 | Schulze et al. | |
| 6,527,711 B1 | 3/2003 | Stivoric et al. | |
| 6,608,562 B1 | 8/2003 | Kimura et al. | |
| 6,656,151 B1 | 12/2003 | Blatter | |
| 6,725,072 B2 | 4/2004 | Steuer et al. | |
| 6,748,254 B2 | 6/2004 | O'Neil et al. | |
| 6,995,665 B2 | 2/2006 | Appelt et al. | |
| 6,997,879 B1 | 2/2006 | Turcott | |
| 7,018,338 B2 | 3/2006 | Vetter et al. | |
| 7,113,815 B2 | 9/2006 | O'Neil et al. | |
| 7,144,375 B2 | 12/2006 | Kosuda | |
| 7,336,982 B2 | 2/2008 | Yoo | |
| 7,378,954 B2 | 5/2008 | Wendt | |
| 7,438,688 B2 | 10/2008 | Kobayashi et al. | |
| 7,539,533 B2 | 5/2009 | Tran | |
| 7,962,308 B2 | 6/2011 | Makino | |
| 8,055,469 B2 | 11/2011 | Kulach et al. | |
| 8,109,874 B2 | 2/2012 | Kong et al. | |
| 8,386,008 B2 | 2/2013 | Yuen et al. | |
| 8,923,941 B2 | 12/2014 | LeBoeuf et al. | |
| 9,005,129 B2 | 4/2015 | Venkatraman et al. | |
| 9,044,180 B2 | 6/2015 | LeBoeuf et al. | |
| 9,687,162 B2 | 6/2017 | Vetter et al. | |
| 9,717,412 B2 | 8/2017 | Roham et al. | |
| 9,797,920 B2 | 10/2017 | Kahn et al. | |
| 10,390,762 B2 | 8/2019 | Romesburg | |
| 10,856,813 B2 | 12/2020 | LeBoeuf et al. | |
| 2002/0013538 A1 | 1/2002 | Teller | |
| 2003/0065269 A1 | 4/2003 | Vetter et al. | |
| 2003/0109791 A1 | 6/2003 | Kondo et al. | |
| 2003/0176815 A1 | 9/2003 | Baba et al. | |
| 2003/0233051 A1 | 12/2003 | Verjus et al. | |
| 2003/0236647 A1 | 12/2003 | Yoon et al. | |
| 2004/0004547 A1 | 1/2004 | Appelt et al. | |
| 2004/0039254 A1 | 2/2004 | Stivoric et al. | |
| 2004/0054291 A1 | 3/2004 | Schulz et al. | |
| 2004/0059236 A1 | 3/2004 | Margulies et al. | |
| 2004/0186387 A1 | 9/2004 | Kosuda et al. | |
| 2004/0186695 A1 | 9/2004 | Aoshima et al. | |
| 2004/0178913 A1 | 11/2004 | Penuela et al. | |
| 2004/0236233 A1 | 11/2004 | Kosuda et al. | |
| 2004/0242976 A1 | 12/2004 | Abreu | |
| 2004/0254501 A1 | 12/2004 | Mault | |
| 2005/0007582 A1 | 1/2005 | Villers et al. | |
| 2005/0043652 A1 | 2/2005 | Lovett et al. | |
| 2005/0059870 A1 | 3/2005 | Aceti | |
| 2005/0192516 A1 | 9/2005 | Takiguchi et al. | |
| 2005/0209516 A1 | 9/2005 | Fraden | |
| 2005/0228463 A1 | 10/2005 | Mac et al. | |
| 2005/0245839 A1 | 11/2005 | Stivoric et al. | |
| 2006/0064037 A1 | 3/2006 | Shalon et al. | |
| 2006/0084879 A1 | 3/2006 | Nazarian et al. | |
| 2006/0178588 A1 | 8/2006 | Brody | |
| 2006/0258927 A1 | 11/2006 | Edgar, Jr. et al. | |
| 2007/0016086 A1 | 1/2007 | Inukai et al. | |
| 2007/0116314 A1 | 5/2007 | Grilliot et al. | |
| 2007/0135717 A1 | 6/2007 | Uenishi et al. | |
| 2008/0076972 A1 | 3/2008 | Dorogusker et al. | |
| 2008/0081972 A1 | 4/2008 | Debreczeny | |
| 2008/0132798 A1 | 6/2008 | Hong et al. | |
| 2008/0146890 A1 | 6/2008 | LeBoeuf et al. | |
| 2008/0154098 A1 | 6/2008 | Morris et al. | |
| 2008/0177162 A1 | 7/2008 | Bae et al. | |
| 2008/0269625 A1 | 10/2008 | Halperin et al. | |
| 2009/0010461 A1 | 1/2009 | Klinghult et al. | |
| 2009/0023556 A1 | 1/2009 | Daly | |
| 2009/0097689 A1 | 4/2009 | Prest et al. | |
| 2009/0105556 A1 | 4/2009 | Fricke et al. | |
| 2009/0112111 A1 * | 4/2009 | Shimizu ................ | A61B 5/024 600/520 |
| 2009/0131761 A1 | 5/2009 | Moroney, III et al. | |
| 2009/0281435 A1 | 11/2009 | Ahmed et al. | |
| 2009/0306736 A1 | 12/2009 | Dobak, III | |
| 2010/0189209 A1 | 7/2010 | O'Rourke | |
| 2010/0217099 A1 | 8/2010 | LeBoeuf et al. | |
| 2010/0274109 A1 | 10/2010 | Hu et al. | |
| 2011/0022352 A1 | 1/2011 | Fujita et al. | |
| 2011/0178759 A1 | 7/2011 | Uchida | |
| 2012/0197093 A1 | 8/2012 | LeBoeuf et al. | |
| 2012/0303319 A1 | 11/2012 | Kirkeby | |
| 2013/0006583 A1 | 1/2013 | Weast et al. | |
| 2013/0178958 A1 | 7/2013 | Kulach | |
| 2017/0112447 A1 | 4/2017 | Aumer et al. | |

FOREIGN PATENT DOCUMENTS

| | | |
|---|---|---|
| CN | 101910846 A | 12/2010 |
| CN | 101980659 A | 2/2011 |
| CN | 102168986 A | 8/2011 |
| CN | 102297701 A | 12/2011 |
| CN | 102435203 A | 5/2012 |
| EP | 0729726 A2 | 9/1996 |
| EP | 1354553 A1 | 10/2003 |
| EP | 2229880 A1 | 9/2010 |
| EP | 2182839 B1 | 10/2011 |
| JP | H10258039 A | 9/1998 |
| JP | 2004283228 A | 10/2004 |
| JP | 2004358271 A | 12/2004 |
| WO | 0021435 A1 | 4/2000 |
| WO | 2005010568 A2 | 2/2005 |
| WO | 2007013054 A1 | 2/2007 |
| WO | 2007122375 A2 | 11/2007 |
| WO | 2011026669 A1 | 3/2011 |
| WO | 2011105914 A1 | 9/2011 |
| WO | 2013038296 A1 | 3/2013 |
| WO | 2013109390 A1 | 7/2013 |
| WO | 2014109982 A2 | 7/2014 |

OTHER PUBLICATIONS

Pierpont et al. 2004 Am. J. Cardiol. 94:64-68 (Year: 2004).*
Buchanan, T., et al., "Neuromusculoskeletal Modeling: Estimation of Muscle Forces and Joint Moments and Movements From Measurements of Neural Command," J Appl Biomech, vol. 20, No. 4, Nov. 1, 2004, pp. 1-34.
Stolwijk, J., "Mathematical Models of Thermal Regulation," Annals of the New York Academy of Sciences, vol. 335, No. 1, Jan. 1, 1980, pp. 98-106.

(56) References Cited

OTHER PUBLICATIONS

Wiggs, L., et al., "Sleep patterns and sleep disorders in children with autistic spectrum disorders: insights using parent report and actigraphy," Developmental Medicine and Child Neurology 2004, vol. 46, No. 6, Jan. 1, 2004, pp. 372-380.

Hastings, P.C., "Symptom burden of sleep-disordered breathing in mild-to-moderate congestive heart failure patients," European Respiratory Journal, vol. 27, No. 4, Jan. 1, 2006, pp. 748-755.

Carskadon, M., et al., "Chapter 2—Normal Human Sleep: an Overview," Monitoring and staging human sleep, from Principles and practice of sleep medicine, 5th edition, St Louis: Elsevier Saunders, Jan. 1, 2011, pp. 1-21.

Critchley, H, "Electrodermal Responses: What Happens in the Brain," The Neuroscientist, vol. 8, No. 2, Jan. 1, 2002, pp. 132-142.

Lang, P., et al., "Looking at pictures: Affective, facial, visceral, and behavioral reactions," Psychophysiology, vol. 30, No. 3, Apr. 22, 1992, pp. 261-273.

Soleymani, M., et al., "Affective Ranking of Movie Scenes Using Physiological Signals and Content Analysis," Proc. 2nd ACM Work. Multimed. Semant., Jan. 1, 2008, pp. 1-8.

Appelhans, B., et al., "Heart Rate Variability as an Index of Regulated Emotional Responding," Review of General Psychology, vol. 10, No. 3, Sep. 15, 2005, pp. 229-240.

Postma, D.S., et al., "The natural history of chronic obstructive pulmonary disease," European Respiratory Monograph, vol. 38, Jan. 1, 2006, pp. 71-83.

Bidargaddi, N., et al., "Ambulatory monitor derived clinical measures for continuous assessment of cardiac rehabilitation patients in a community care model," Pervasive Computing Technologies for Healthcare, 2008 Second International Conference on Pervasive Computing Technolovies for Healthcare, Jan. 30, 2008, pp. 1-5.

Hertzman, A., "The Blood Supply of Various Areas as Estimated by the Photoelectric Plethysmograph," Am J. Physiol, vol. 124, Issue 2, Jul. 18, 1938, pp. 328-340.

Hayes, M., et al., "Artifact reduction in photoplethysmography," Applied Optics, vol. 37, No. 31, Nov. 1, 1998, pp. 7437-7446.

Page, E., et al., "Physiological approach to monitor patients in congestive heart failure: application of a new implantable device-based system to monitor daily life activity and ventilation," Eurospace, vol. 9, May 3, 2007, pp. 687-693.

Moy, M., et al., "Free-living physical activity in COPD: Assessment with accelerometer and activity checklist," Journal of Rehabilitation Research & Development, vol. 46, No. 2, Nov. 2, 2009, pp. 277-286.

Bennett, T., et al., "Development of Implantable Devices for Continuous Ambulatory Monitoring of Central Hemodynamic Values in Heart Failure Patients," Pacing Clin Electrophysiol. Jun. 2005; vol. 28, No. 6, Jun. 1, 2005, pp. 573-584.

Allen, J., "Photoplethysmography and its application in clinical physiological measurement," Physiological Measurement, vol. 28, Feb. 20, 2007, pp. 1-39.

Webster, J.G. (ed.), "Design of Pulse Oximeters," Institute of Physics Publishing, Philadelphia, PA, Jan. 1, 1997, pp. 1-134.

Webster, J.G. (ed.), "Design of Pulse Oximeters," Institute of Physics Publishing, Philadelphia, PA, Jan. 1, 1997, pp. 135-267.

Shevchenko, Y, et al., "90th Anniversary of the Development by Nikolai S. Korotkoff of the Ascultatory Method of Measuring Blood Pressure," Circulation, vol. 94, No. 2, Jul. 15, 1996, pp. 116-118.

Han, H., et al., "Development of a wearable monitoring device with motion artifact reduced algorithm," International Conference on Control, Automation and Systems 2007, Oct. 17, 2007, Seoul, Korea, pp. 1581-1584.

Petition for Inter Partes Review of U.S. Pat. No. 8,157,730; *Apple, Inc.* (Petitioner) v. *Valencell, Inc.* (Patent Owner), IPR 2017-01701, filed Jun. 30, 2017, pp. 1-89.

Petition for Inter Partes Review of U.S. Pat. No. 8,652,040; *Apple, Inc.* (Petitioner) v. *Valencell, Inc.* (Patent Owner), IPR 2017-01702, filed Jun. 30, 2017, pp. 1-70.

Petition for Inter Partes Review of U.S. Pat. No. 8,652,040; *Apple, Inc.* (Petitioner) v. *Valencell, Inc.* (Patent Owner), IPR 2017-01703, filed Jun. 30, 2017, pp. 1-79.

Petition for Inter Partes Review of U.S. Pat. No. 8,888,701; *Apple, Inc.* (Petitioner) v. *Valencell, Inc.* (Patent Owner), IPR 2017-01704, filed Jun. 30, 2017, pp. 1-84.

Declaration of Dr. Majid Sarrafzadeh, Exhibit 1003, Petition for Inter Partes Review of U.S. Pat. No. 8,888,701; *Apple, Inc.* (Petitioner) v. *Valencell, Inc.* (Patent Owner), IPR 2017-01704, filed Jun. 30, 2017, pp. 1-109.

Declaration of Brian W. Anthony, Ph.D. in Support of Petition for Inter Partes Review of U.S. Pat. No. 8,157,730, Exhibit 1003, Petition for Inter Partes Review of U.S. Pat. No. 8,157,730 *Apple, Inc.* (Petitioner) v. *Valencell, Inc.* (Patent Owner), IPR 2017-01701, filed Jun. 30, 2017, pp. 1-138.

Declaration of Dr. Majid Sarrafzadeh, Exhibit 1003, Petition for Inter Partes Review of U.S. Pat. No. 8,652,040; *Apple, Inc.* (Petitioner) v. *Valencell, Inc.* (Patent Owner), IPR 2017-01703, filed Jun. 30, 2017, pp. 1-87.

Declaration of Dr. Majid Sarrafzadeh, Exhibit 1003, Petition for Inter Partes Review of U.S. Pat. No. 8,652,040; *Apple, Inc.* (Petitioner) v. *Valencell, Inc.* (Patent Owner), IPR 2017-01702, filed Jun. 30, 2017, pp. 1-92.

Declaration of Brian W. Anthony, Ph.D. in Support of Petition for Inter Partes Review of U.S. Pat. No. 9,044,180, Exhibit 1003, Petition for Inter Partes Review of U.S. Pat. No. 9,044,180 *Apple, Inc.* (Petitioner) v. *Valencell, Inc.* (Patent Owner), IPR 2017-01947, filed Aug. 2-17, 15, pp. 1-153.

Mendelson, J., et al., "Measurement Site and Photodetector Size Considerations iin Optimizing Power Consumption of a Wearable Reflectance Pulse Oximeter", Proceedings of the 25th Annual International Conference of the IEEE EMBS, Engineering in Medicine and Biology Society, Cancun, Mexico, Sep. 17, 2003, pp. 1-4.

Palder, et al., "Vascular Access for Hemodialysis, Patency rates and Results of Revision", Annals of Surgery, vol. 202, No. 2, Aug. 1, 1985, pp. 1-5.

Spigulis, J., et al., "Wearable wireless photoplethysmography sensors," Biophotonics: Photonic Solutions for Better Health Care, Proceedings of SPIE, vol. 6991, May 1, 2008, pp. 1-7.

Sandberg, M., et al., "Non-invasive monitoring of muscle blood perfusion by photoplethysmography: evaluation of a new application," Acta Physiol Scand., vol. 183, No. 4, Dec. 7, 2004, pp. 335-343.

Sum, K.W., et al. "Vital Sign Monitoring for Elderly at Home: Development of a Compound Sensor for Pulse Rate and Motion," Studies in Health Technology and Informatics, Personalised Health Management Systems, IOS Press, Jan. 1, 2005, pp. 43-50.

Mendelson, Y., et al., "A Wearable Reflectance Pulse Oximeter for Remote Physiological Monitoring," Proceedings of the 28th IEEE EMBS Annual International Conference New York City, USA, Aug. 30, 2006, pp. 912-915.

Jung, W., "Chapter H: OP Amp History," Op Amp Applications Handbook, published by Newnes/Elsevier, Jan. 1, 2005, ISBN-0-7506-7844-5, pp. H.1-H.72.

Texas Instruments, "General Purpose Operational Amplifiers", SLOSS094B, Nov. 1, 1970, pp. 1-19.

Schmitt, O., "A simple differential amplifier," Review of Scientific Instruments vol. 8, No. 126, Apr. 1, 1937, American Institute of Physics, pp. 1-3, available at: http://dx.doi.org/10.1063/1.1752256.

Gray, p, et al., "Recent Advances in Monolithic Operational Amplifier Design," IEEE Transactions on Circuits and Systems, vol. CAS-21, No. 3, May 1, 1974, pp. 317-327.

Horowitz, P., et al., "The Art of Electronics," Second Edition, Cambridge University Press, Jan. 1, 1989, pp. 98-102.

Petition for Inter Partes Review of U.S. Pat. No. 9,044,180; *Apple, Inc.* (Petitioner) v. *Valencell, Inc.* (Patent Owner), IPR 2017-01947, filed Aug. 15, 2017, pp. 1-86.

Asada, H., et al., "Mobile Monitoring with Wearable Photoplethysmographic Biosensors," IEEE Engineering in Medicine and Biology Magazine, May/Jun. 2003 Issue, May 1, 2003, pp. 28-40.

(56) References Cited

OTHER PUBLICATIONS

Wang, L et al. "Multichannel Reflective PPG Earpiece Sensor with Passive Motion Cancellation," IEEE Transactions on Biomedical Circuits and Systems, vol. 1, No. 4, Dec. 1, 2007, pp. 235-241.

Bumgardner, W., "Top 8 Walking Speedometers and Odometers", retrieved on Jun. 18, 2014, retrieved from internet: http://walking.about.com/od/measure/tp/speedometer.htm.

Garmin, "Running Watches Heart Rate Monitor", Swim Watch, Heart Rate Monitors Reviews, Oct. 12, 2010, retrieved from internet: http://web.archive.org/web/*/http://heartratemonitors-reviews.com/category/swim-watch/.

Han et al. "Artifacts in wearable photoplethysmographs during daily life motions and their reduction with least mean square based active noise cancellation method," Computers in Biology and Medicine 42 (2012), Published Dec. 27, 2011, Elsevier Ltd., pp. 387-393.

Poh, Ming-Zher et al., "Non-contact, automated cardiac pulse measurements using video imaging and blind source separation." Optics Express, vol. 18, No. 10, May 7, 2010, pp. 1-13.

Wise, K., "Integrated sensors, MEMS, and microsystems: Reflections on a fantastic voyage," Sensors and Actuators A, vol. 136, Feb. 5, 2007, pp. 39-50.

Gigoi, B.P., et al., "Integration Technology for MEMS Automotive Sensors," 28th Annual Conference of the IEEE, Jan. 1, 2002, pp. 2712-2717.

Ko, W., "Trends and frontiers of MEMS," Sensors and Actuators A, vol. 136, Feb. 1, 2007, pp. 62-67.

Barbour, N., "Inertial Sensor Technology Trends," IEEE Sensors Journal, vol. 1, No. 4, Dec. 1, 2001, pp. 332-339.

Vigario, R., "Independent Component Approach to the Analysis of EEG and MEG Recordings," IEEE Transactions on Biomedical Engineering, vol. 47, No. 5, May 1, 2000, pp. 589-593.

Mayer-Kress, G., "Localized Measures for Nonstationary Time-Series of Physiological Data," Integr. Physiol. Behav. Sci, vol. 29, No. 3, Jul. 1, 1994, pp. 205-210.

Shaw, G.A., et al., "Warfighter Physiological and Environmental Monitoring: A Study for the U.S. Army Research Institute in Environmental Medicine and the Soldier Systems Center," Lincoln Laboratory, Massachusetts Institute of Technology, Lexington, MA., Nov. 1, 2004, pp. 1-128.

Laguna, P., et al., "Power Spectral Density of Unevenly Sampled Data by Least-Square Analysis: Performance and Application to Heart Rate Signals," IEEE Transactions on Biomedical Engineering, vol. 45, No. 6, Jun. 1, 1998, pp. 698-715.

Richardson, J.E., "Physiological Responses of Firefighters Wearing Level 3 Chemical Protective Suits While Working in Controlled Hot Environments," J. Occup. Environ. Med., vol. 43, No. 12, Dec. 1, 2001, pp. 1064-1072.

Scanlon, M., "Acoustic Sensors in the Helmet Detect Voice and Physiology," Proceedings of SPIE, vol. 5071, Jan. 1, 2003, pp. 41-51.

Arnold, M., et al., "Adaptive AR Modeling of Nonstationary Time Series by Means of Kalman Filtering," IEEE Transactions on Biomedical Engineering, vol. 45, No. 5, May 1, 1998, pp. 553-562.

Yan, Y., et al., "Reduction of motion artifact in pulse oximetry by smoothed pseudo Wigner-Ville distribution," Journal of NeuroEngineering and Rehabilitation, vol. 2, No. 3, Mar. 1, 2005, pp. 1-9.

Lee, C.M., et al., "Reduction of Motion Artifacts from Photoplethysmographic Recordings Using a Wavelet Denoising Approach," IEEE EMBS Asian-Pacific Conference on Biomedical Engineering, Jan. 1, 2003, pp. 194-195.

Foo, J.Y.A., "Comparison of wavelet transformation and adaptive filtering in restoring artefact-induced time-related measurement," Biomedical Signal Processing and Control vol. 1, No. 1 (2006), Mar. 24, 2006, pp. 93-98.

Wood, L., et al., "Active Motion Artifact Reduction for Wearable Sensors Using Laguerre Expansion and Signal Separation," Proceedings of the 2005 IEEE Engineering in Medicine and Biology 27th Annual Conference, Shanghai, China, Sep. 1, 2005, pp. 3571-3574.

Cacioppo, J., "Inferring Psychological Significance From Physiological Signals," American Psychologist, vol. 45, No. 1, American Psychological Association, Jan. 1, 1990, pp. 16-28.

Rhee, S., et al., "Artifact-Resistant Power-Efficient Design of Finger-Ring Plethysmographic Sensors," IEEE Transactions on Biomedical Engineering, vol. 48, No. 7, Jul. 1, 2001, pp. 795-805.

Wagner, J., et al., "From Physiological Signals to Emotions: Implementing and Comparing Selected Methods for Feature Extraction and Classification," IEEE Int. Conf. Multimedia and Expo, Jan. 1, 2005, pp. 1-4.

Parkka, J., et al., "Activity Classification Using Realistic Data From Wearable Sensors," IEEE Transactions on Information Technology in Biomedicine, vol. 10, No. 1, Jan. 1, 2006, pp. 119-128.

Georgoulas, G., et al., "Predicting the Risk of Metabolic Acidosis for Newborns Based on Fetal Heart Rate Signal Classification Using Support Vector Machines," IEEE Transactions on Biomedical Engineering, vol. 53, No. 5, May 1, 2006, pp. 875-884.

Liao, W., et al., "A Real-Time Human Stress Monitoring System Using Dynamic Bayesian Network," Proceedings of the 2005 IEEE Computer Society Conference on Computer Vision and Pattern Recognition, Jan. 1, 2005, pp. 1-8.

Moy, M., et al., "Accuracy of uniaxial accelerometer in chronic obstructive pulmonary disease," Journal of Rehabilitation Research and Development, vol. 45, No. 4, Nov. 4, 2008, pp. 611-618.

Moy, M., et al., "Ambulatory Monitoring of Cumulative Free-Living Activity," IEEE Engineering in Medicine and Biology Magazine May/Jun. 2003, May 1, 2003, pp. 89-95.

Ricke, AD, et al. "Automatic Segmentation of Heart Sound Signals Using Hidden Markov Models," IEEE Computers in Cardiology 2005; vol. 32, Jan. 1, 2005, pp. 953-956.

Acharya, R., et al., "Classification of cardiac abnormalities using heart rate signals," Medical and Biological Engineering and Computing 2004, vol. 42, No. 3, Jan. 1, 2004, pp. 288-293.

Allen, F., et al., "Classification of a known sequence of motions and postures from accelerometry data using adapted Gaussian mixture models," Institute of Physics Publishing Physiological Measurement, vol. 27, No. 10, Jul. 25, 2006, pp. 935-951.

Lee, J., et al., "Design of filter to reject motion artifact of pulse oximetry," Computer Standards & Interfaces, vol. 26 (2004), Jul. 4, 2003, pp. 241-249.

Rezek, I.A., et al., "Stochastic Complexity Measures for Physiological Signal Analysis," IEEE Transactions on Biomedical Engineering, vol. 45, No. 9, Sep. 1, 1998, pp. 1186-1191.

Gibbs, P., et al., "Active motion artifact cancellation for wearable health monitoring sensors using collocated MEMS accelerometers," Smart Struct Mater., International Society for Optics and Photonics, Jan. 1, 2005, pp. 1-9.

Merletti, R., et al., "Advances in processing of surface myoelectric signals: Part 1," Medical and Biological Engineering and Computing, vol. 33, No. 3, May 1, 1995, pp. 362-372.

Asada, H., et al., "Active Noise Cancellation Using MEMS Accelerometers for Motion-Tolerant Wearable Bio-Sensors," Proceedings of the 26th Annual International Conference of the IEEE EMBS, San Francisco, CA, USA, Sep. 1, 2004, pp. 2157-2160.

Newman, A., et al., "Sleep Disturbance, Psychosocial Correlates, and Cardiovascular Disease in 5201 Older Adults: The Cardiovascular Health Study," Journal of American Geriatric Society, vol. 45, No. 1, Jan. 1, 1997, pp. 1-7.

Chan, K.W., et al., "Adaptive Reduction of Motion Artifact from Photoplethysmographic Recordings using a Variable Step-Size LMS Filter," IEEE, Sensors, Jun. 1, 2002, pp. 1342-1346.

Dew, M.A., et al., "Healthy Older Adults' Sleep Predicts All-Cause Mortality at 4 to 19 Years of Follow-Up," Psychosomatic Medicine, vol. 65, Jan. 1, 2003, pp. 63-73.

Gibbs, P., et al., "Reducing Motion Artifact in Wearable Bio-Sensors Using MEMS Accelerometers for Active Noise Cancellation," IEEE American Control Conference, Jun. 1, 2005, pp. 1581-1586.

Yang, B-H, et al., "Development of the ring sensor for healthcare automation," Robotics and Autonomous Systems, vol. 30. Jan. 1, 2000, pp. 273-281.

(56) References Cited

OTHER PUBLICATIONS

Healey, J., et al., "Detecting Stress During Real-World Driving Tasks Using Physiological Sensors," IEEE Transactions on Intelligent Transportation Systems, vol. 6, No. 2, Jun. 1, 2005, pp. 156-166.

Hayes, M.J., et al., "A New Method for Pulse Oximetry Possessing Inherent Insensitivity to Artifact," IEEE Transactions on Biomedical Engineering, vol. 48, No. 4, Apr. 1, 2001, pp. 452-461.

Wilson, G., et al., "An Analysis of Mental Workload in Pilots During Flight Using Multiple Psychophysiological Measures," The International Journal of Aviation Psychology, vol. 12, No. 1, May 1, 2001, pp. 3-18.

Baddeley, A.D., "Selective Attention and Performance in Dangerous Environments," HPEE, vol. 5, No. 1, Oct. 1, 2000, pp. 86-91.

Wilson, G.F., et al., "Performance Enhancement with Real-time Physiologically Controlled Adapative Aiding," Proceedings of the IEA 2000 / HFES 2000 Congress, vol. 44, Jul. 30, 2000, pp. 61-64.

Skinner, M.J., et al., "Workload Issues in Military Tactical Airlift," The International Journal of Aviation Psychology, vol. 12, No. 1, May 1, 2001, pp. 79-93.

Helander, M., "Applicability of Drivers' Electrodermal Response to the Design of the Traffic Environment," Journal of Applied Psychology, vol. 63, No. 4, Jan. 18, 1978, pp. 481-488.

Perala, C.H., "Galvanic Skin Response as a Measure of Soldier Stress," Army Research Laboratory, ARL-TR-4114, May 1, 2007, pp. 1-35.

Zhai, J., et al., "Stress Detection in Computer Users Based on Digital Signal Processing of Noninvasive Physiological Variables," Conf Proc IEEE Eng Med Biol Soc., New York, NY, Aug. 31, 2006; pp. 1355-1358.

Zhai, J., et al., "Stress Recognition Using Non-invasive Technology," FLAIRS Conference, Melbourne Beach, Florida, May 11, 2006, AAAI Press, pp. 395-401.

Endler, J., "Signals, Signal Conditions, and the Direction of Evolution," The American Naturalist, vol. 139, Supplement, Mar. 1, 1992, pp. S125-S153.

Sadeh, A., "The role of actigraphy in sleep medicine," Sleep Medicine Reviews, vol. 6, No. 2, Jan. 1, 2002, pp. 113-124.

\* cited by examiner

PHYSIOLOGICAL METRIC ESTIMATION RISE AND FALL LIMITING

This application is a continuation of prior U.S. patent application Ser. No. 14/370,658, filed 3 Jul. 2014, which was the National Stage of International Application No. PCT/US2012/071593, filed 24 Dec. 2012, which claims the benefit of U.S. Provisional Application Ser. No. 61/586,874, filed 16 Jan. 2012, the disclosures of all of which are incorporated by reference herein in their entirety.

The embodiments disclosed herein generally relate to photoplethysmograph (PPG) sensors for monitoring heart rate and other physiological metrics, and more particularly relate to noise reduction techniques for PPG sensors.

BACKGROUND

Personal health monitors provide users with the ability to monitor their overall health and fitness by enabling the user to monitor heart rate or other physiological information during exercise, athletic training, rest, daily life activities, physical therapy, etc. Such devices are becoming increasingly popular as they become smaller and more portable.

A heart rate monitor represents one example of a personal health monitor. A common type of heart rate monitor uses a chest strap monitor that includes surface electrodes to detect muscle action potentials from the heart. Because such surface electrodes provide a relatively noise free signal, the information produced by monitors that use surface electrodes is highly accurate. However, most users find chest strap monitors uncomfortable and inconvenient.

Another type of heart rate monitor uses PPG sensors disposed in an ear bud. The ear provides an ideal location for a monitor because it is a relatively immobile platform that does not obstruct a person's movement or vision. PPG sensors proximate the ear have, e.g., access to the inner ear canal and tympanic membrane (for measuring core body temperature), muscle tissue (for monitoring muscle tension), the pinna and earlobe (for monitoring blood gas levels), the region behind the ear (for measuring skin temperature and galvanic skin response), and the internal carotid artery (for measuring cardiopulmonary functioning). The ear is also at or near the point of the body's exposure to environmental breathable toxins of interest (volatile organic compounds, pollution, etc.), noise pollution experienced by the ear, lighting conditions for the eye, etc. Further, as the ear canal is naturally designed for transmitting acoustical energy, the ear provides a good location for monitoring internal sounds, such as the heartbeat, breathing rate, mouth motion, etc.

PPG sensors measure the relative blood flow using an infrared or other light source that projects light that is ultimately transmitted through or reflected off tissue, and is subsequently detected by a photodetector and quantified. For example, higher blood flow rates result in more light being scattered by the blood, which ultimately increases the intensity of the light that reaches the photodetector. By processing the signal output by the photodetector, a monitor using PPG sensors may measure the blood volume pulse (the phasic change in blood volume with each heartbeat), the heart rate, heart rate variability, and other physiological information. PPG sensors are generally small and may be packaged such that they do not encounter the comfort and/or convenience issues associated with other conventional health monitors. However, PPG sensors are also more sensitive to motion artifact noise than are many other types of sensors, and thus are more prone to accuracy problems.

SUMMARY

The filtering techniques disclosed herein improve the accuracy of a heart rate and/or other physiological metrics provided by a monitor, e.g., one using photoplethysmograph (PPG) sensors. In general, the disclosed filtering technique improves the accuracy by adjusting an estimate of a heart rate as a function of a rate limit associated with the heart rate.

One exemplary method processes data provided by a physiological sensor, e.g., a PPG sensor, to reduce the noise and therefore improve the accuracy of a physiological metric, e.g., a heart rate. The method comprises determining, based on a physiological waveform received from a physiological sensor, an instantaneous estimate of a physiological metric, and comparing the instantaneous estimate to a current filtered estimate of the physiological metric. The method further includes computing a revised filtered estimate of the physiological metric as a function of the current filtered estimate and a rate limit based on the comparison between the instantaneous estimate and the current filtered estimate, and outputting the revised filtered estimate.

One exemplary physiological processor processes data provided by a physiological sensor, e.g., a PPG sensor, to reduce the noise and therefore improve the accuracy of a physiological metric, e.g., a heart rate. The processor comprises a spectral transformer and a filter. The spectral transformer is configured to determine, based on a received waveform, an instantaneous estimate of the physiological metric. The filter is configured to compare the instantaneous estimate to a current filtered estimate of the physiological metric, and output a revised filtered estimate of the physiological metric computed as a function of the current filtered estimate and a rate limit based on the comparison between the instantaneous estimate and the current filtered estimate.

DETAILED DESCRIPTION

Many of the embodiments disclosed herein are derived from new findings on how vital signs, PPG signals, and acceleration changes within the human body during activity. By understanding the relationship between these changes, a method has been invented to track heart rate and other vital signs in the midst of motion artifact noise and other types of noise that may otherwise lead to erroneous estimations of heart rate and other vital signs.

Figure 1:
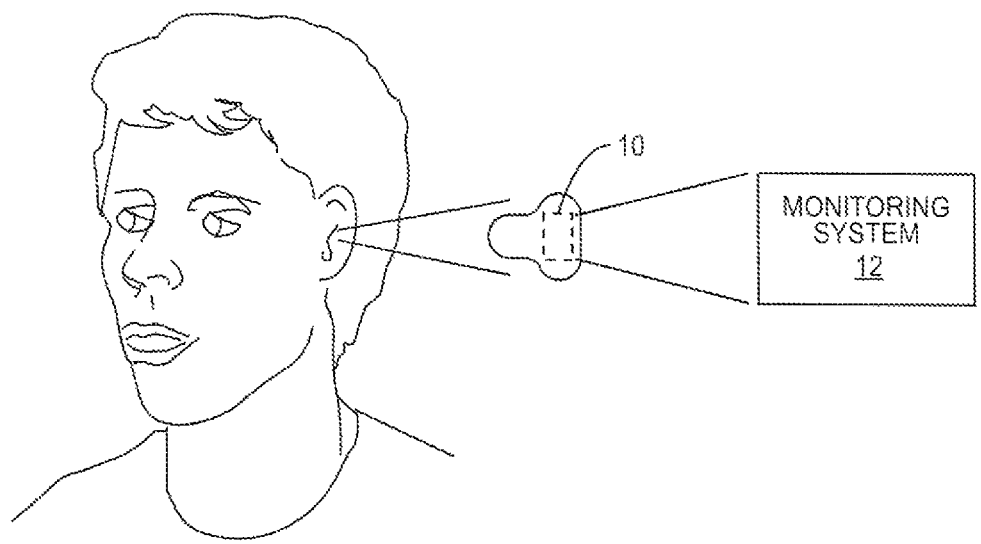
FIG. 1 shows an exemplary heart rate monitor disposed in an ear bud.

The filtering technique disclosed herein improves the accuracy of the results achieved when processing data, e.g., heart rate data, provided by a physiological sensor. FIG. 1 shows an exemplary monitoring system 12 disposed in an ear bud 10. The ear bud 10 may comprise a wireless or wired ear bud that communicatively couples to a remote device, e.g., a music player, a smart phone, a personal data assistant, etc. The monitoring system 12 monitors the heart rate and/or other physiological metrics, and outputs such physiological information to the user and/or to other processing functions. While the monitoring system 12 disclosed herein is presented as being part of an ear bud 10, it will be appreciated that monitoring system 12 may be disposed into any device that secures to the body of a user, e.g., a device that secures to an ear, finger, toe, limb (arm, leg, ankle, etc.), wrist, nose, etc. In some embodiments, the device may comprise a patch, e.g., a bandage, designed to attach the system 12 to any desired location on the user's body.

Figure 2:
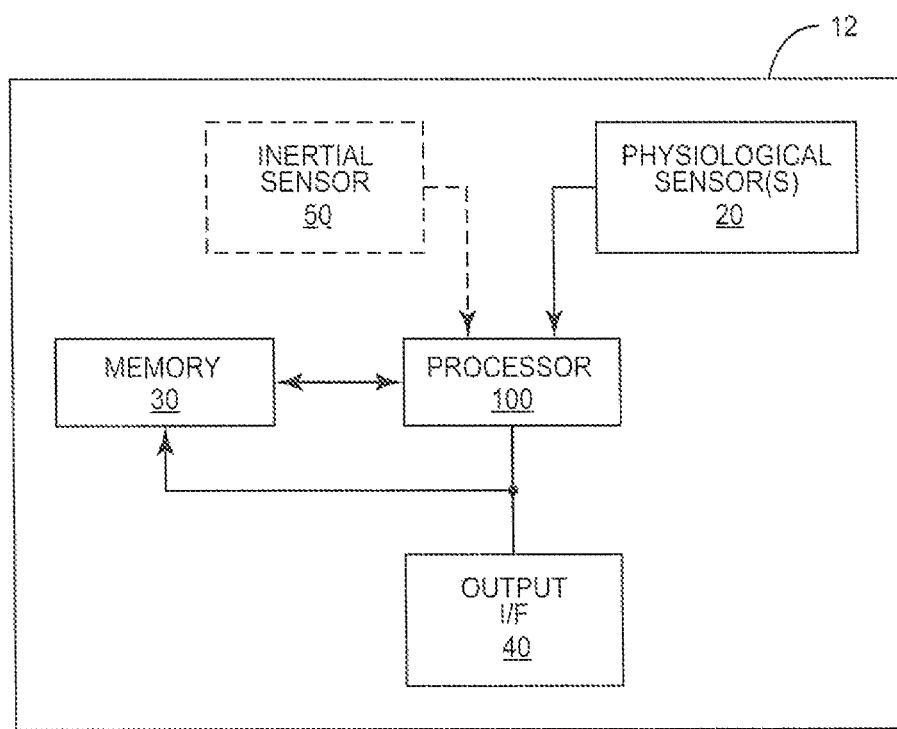
FIG. 2 shows a block diagram of an exemplary physiological monitoring system disposed in a housing.

FIG. 2 shows a block diagram of an exemplary monitoring system 12 according to one exemplary embodiment. System 12 comprises a processor 100 coupled to one or more physiological sensors 20, a memory 30, and an output interface 40. As discussed further herein, system 12 may also include an optional inertial sensor 50 configured to sense energy, e.g., motion, external to the system 12. Physiological sensor(s) 20 produce a physiological waveform responsive to the physiological state of the user. Processor 100 processes the physiological waveform using the filtering technique disclosed herein, along with information stored in memory 30, to determine a heart rate and/or one or more physiological metrics with improved accuracy. Output interface 40 outputs the determined physiological metric(s). It will be appreciated that output interface may comprise a transceiver for transmitting the data output by the processor 100 to a remote device. Alternatively or additionally, the output interface may provide the output data to a user interface, e.g., a display, a database, another processor, and/or a processing function.

In exemplary embodiments, the physiological sensors 20 comprise photoplethysmograph (PPG) sensors that generate an electrical physiological waveform responsive to detected light intensity. PPG sensors comprise light intensity sensors that generally rely on optical coupling of light into the blood vessels. As used herein, the term "optical coupling" refers to the interaction or communication between excitation light entering a region and the region itself. For example, one form of optical coupling may be the interaction between excitation light generated from within a light-guiding ear bud 10 and the blood vessels of the ear. Light guiding ear buds are described in co-pending U.S. Patent Application Publication No. 2010/0217102, which is incorporated herein by reference. In one embodiment, the interaction between the excitation light and the blood vessels may involve excitation light entering the ear region and scattering from a blood vessel in the ear such that the intensity of the scattered light is proportional to blood flow within the blood vessel. Another form of optical coupling may result from the interaction between the excitation light generated by an optical emitter within the ear bud and the light-guiding region of the ear bud.

Processor 100 determines one or more physiological metrics from the physiological waveform and filters the determined metric(s) to produce a revised physiological metric having an improved accuracy. The determined physiological metric may also refer to a physiological assessment computed from one or more physiological metrics. For simplicity, the following describes the processor 100 in terms of determining a heart rate. However, the processor 100 may alternatively or additionally determine other physiological metrics, e.g., a respiration rate, a heart rate variability (HRV), a pulse pressure, a systolic blood pressure, a diastolic blood pressure, a step rate, an oxygen uptake ($VO_2$), an R-R interval (which represents the interval between successive R-peaks in an ECG waveform), a maximal oxygen uptake ($VO_2$ max), calories burned, trauma, cardiac output and/or blood analyte levels including percentage of hemoglobin binding sites occupied by oxygen ($SPO_2$), percentage of methomoglobins, a percentage of carbonyl hemoglobin, and/or a glucose level. Alternatively or additionally, processor 100 may determine and filter one or more physiological assessments, e.g., a ventilatory threshold, lactate threshold, cardiopulmonary status, neurological status, aerobic capacity ($VO_2$ max), and/or overall health or fitness. Though heart rate is used as an example of a specific physiological metric that may be accurately extracted using the embodiments disclosed herein, it should be understood that other physiological metrics may also be derived using these embodiments. Periodically changing vital signs, such as, but not limited to, heart rate, respiration rate, R-R interval, circadian changes, blood-gas level changes, and the like may be particularly suited for signal extraction under the described embodiments.

Figure 3:
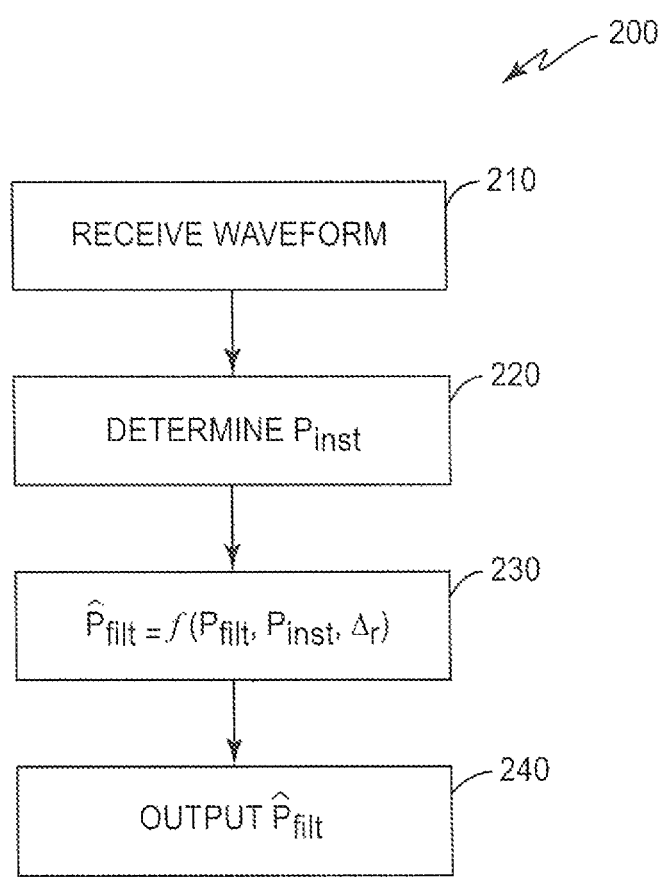
FIG. 3 shows an exemplary process for determining physiological information from data provided by a physiological sensor.

FIG. 3 shows an exemplary method 200 that may be implemented by processor 100 to compute a revised heart rate. After processor 100 receives the physiological waveform from the sensor(s) 20 (block 210), the processor 100 determines an instantaneous estimate $P_{inst}$ of the heart rate. After comparing $P_{inst}$ to a current filtered estimate $P_{filt}$, which may be retrieved from memory 30, processor 100 computes a revised filtered estimate $\hat{P}_{filt}$ of the heart rate as a function of $P_{filt}$ and a rate limit $\Delta_r$ based on the comparison (block 230), where $\Delta_r$ may also be retrieved from memory 30. Processor 100 subsequently outputs the revised filtered estimate $\hat{P}_{filt}$ to output 40 (block 240). It will be appreciated that processor 100 may also store the revised filtered estimate $\hat{P}_{filt}$ in memory 30, e.g., so that it may be used in subsequent calculations and/or as a current filtered estimate $P_{filt}$. As used herein, the rate limit represents a limit to the rate of change for the heart rate. For example, the rate limit may represent the rate of change in beats per minute (BPM) that the heart rate may experience in a 1 second frame period. Such a rate limit may be determined based on empirical evidence, and is generally predetermined. It will be appreciated that the rate limit may be expressed as the rate of change experienced for any length frame period, where for example, the rate limit in BPM/s is multiplied by the length of the frame period (in seconds).

Figure 4:
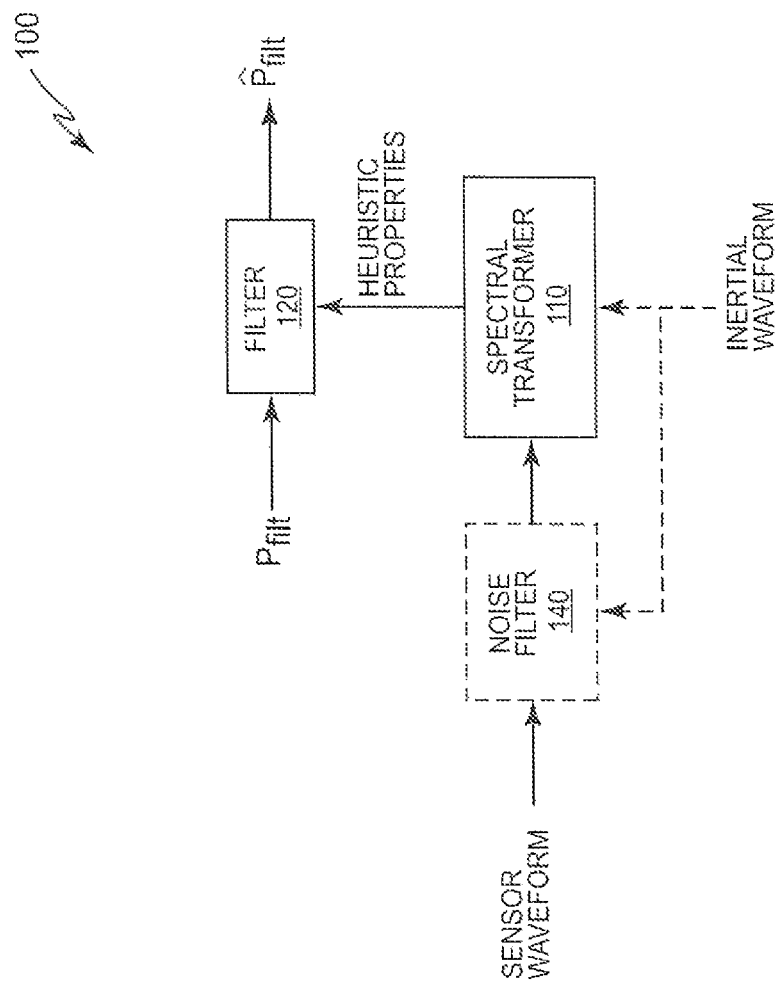
FIG. 4 shows an exemplary block diagram for the processor of FIG. 2, as configured to implement the process of FIG. 3.

FIG. 4 shows a block diagram of an exemplary processor 100 configured to process the physiological waveform provided by the sensor(s) 20. Processor 100 comprises a spectral transformer 110 and a filter 120. Spectral transformer 110 spectrally transforms the physiological waveform received from the sensor(s) 20 to determine one or more heuristic properties of the physiological waveform and provides the heuristic properties to the filter 120. For example, the spectral transformer 110 may evaluate the spectrally transformed waveform to identify the spectral peak having the largest amplitude. The spectral transformer 110 then defines the frequency of the peak with the largest amplitude as the instantaneous estimate $P_{inst}$ of the heart rate. Filter 120 filters the instantaneous estimate $P_{inst}$ of the heart rate to compute the revised filter estimate $\hat{P}_{filt}$ as a function of $P_{filt}$ and $\Delta_r$ based on a comparison between $P_{filt}$ and $P_{inst}$.

Figure 5:
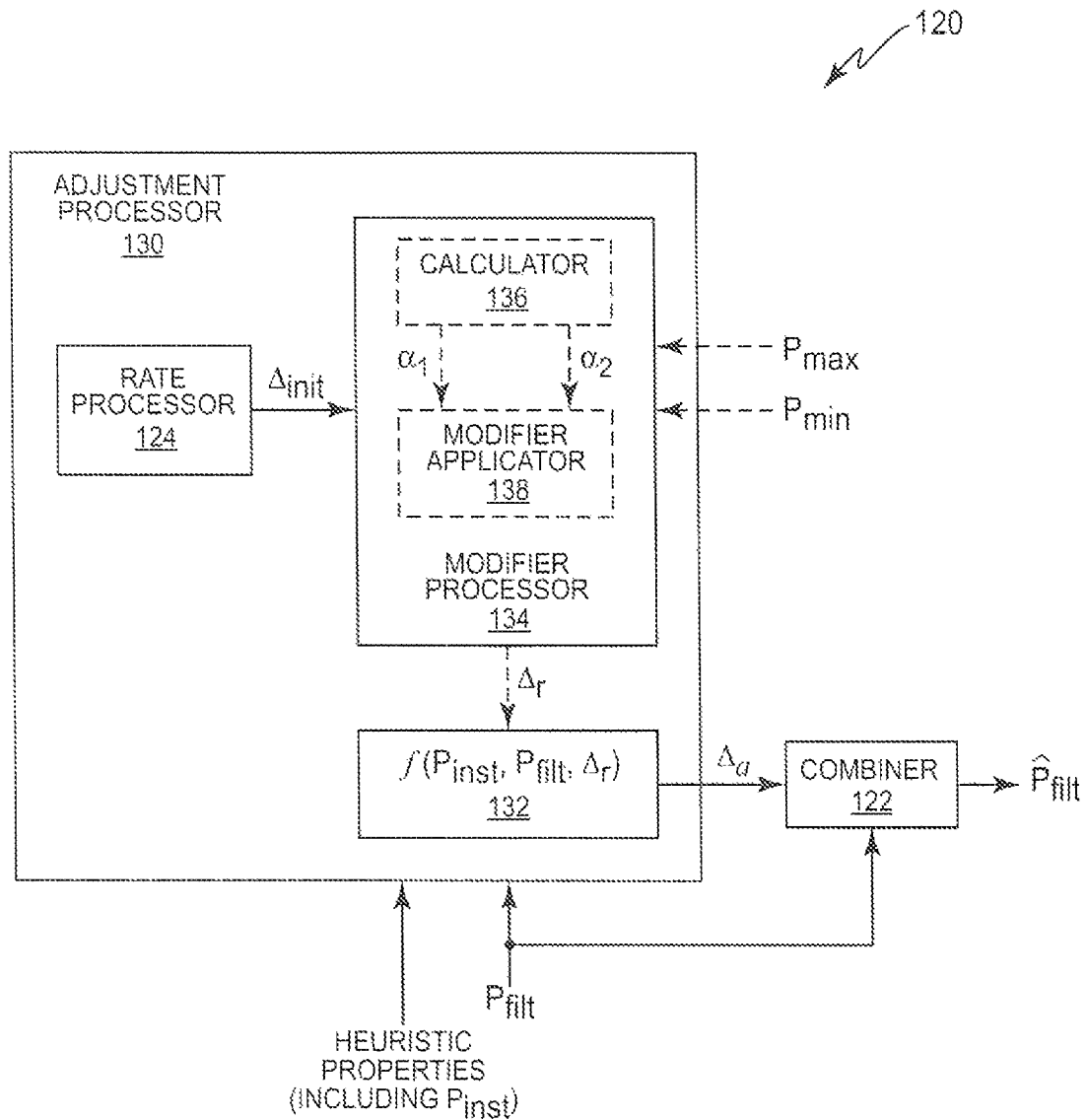
FIG. 5 shows an exemplary block diagram for the filter of FIG. 4.

To illustrate, consider the following example. If the instantaneous heart rate is greater than or equal to the current filtered heart rate, filter 120 may compute the revised filter estimate as a function of a rising/increasing heart rate limit $\Delta_{r+}$ and the current filtered heart rate, e.g., according to:

$$\hat{P}_{filt} = P_{filt} + \min(\Delta_{r+}, P_{inst} - P_{filt}), \quad (1)$$

where, the rising heart rate limit $\Delta_{r+}$ is, e.g., 6 BPM in a 1 second frame period. If, however, the instantaneous heart rate is less than the current filtered heart rate, filter 120 may compute the revised filter estimate as a function of a falling heart rate limit $\Delta_{r-}$ and the current filtered heart rate, e.g., according to:

$$\hat{P}_{filt} = P_{filt} + \max(\Delta_{r-}, P_{inst} - P_{filt}), \quad (2)$$

where, the falling heart rate limit $\Delta_{r-}$ is, e.g., −4.

t FIG. 5 shows a block diagram of an exemplary filter 120. In one embodiment, filter 120 comprises an adjustment processor 130 and a combiner 122. Combiner 122 combines an adjustment parameter $\Delta_a$ output by adjustment processor 130 with $P_{filt}$ to compute the revised filtered estimate $\hat{P}_{filt}$ of the heart rate. Adjustment processor 130 comprises a function processor 132 configured to compute $\Delta_a$ as a function of the rate limit $\Delta_r$ and the current filtered estimate $P_{filt}$ responsive to the comparison between the instantaneous estimate $P_{inst}$ and the current filtered estimate $P_{filt}$. Using the previous example, when $P_{inst} \geq P_{filt}$, function processor 132 may compute the adjustment parameter $\Delta_a$ according to:

$$\Delta_a = \min(\Delta_{r+}, P_{inst} - P_{filt}) \quad (3)$$

If, however $P_{inst} < P_{filt}$, function processor 132 may compute the adjustment parameter $\Delta_a$ according to:

$$\Delta_a = \max(\Delta_{r-}, P_{inst} - P_{filt}). \quad (4)$$

In some embodiments, adjustment processor 130 selects either the rising or falling rate limit used by function processor 132 based on the comparison between the instantaneous estimate and the current filtered estimate. Alternatively, filter 120 may include a rate processor 124 that selects an initial rate limit $\Delta_{init}$, which may comprise the rising or falling rate limit, based on the comparison between the instantaneous estimate and the current filtered estimate. In still another embodiment, the function processor 132 may comprise different processing paths associated with different comparison results, where adjustment processor 130 selects one of the processing paths based on the comparison between the instantaneous estimate and the current filtered estimate, where each processing path is associated with a different one of Equations (1)/(3) and (2)/(4), and where each processing path includes the corresponding rate limit.

It will also be appreciated that the different values disclosed herein for the rising and falling rate limits are exemplary and non-limiting. In some embodiments, the magnitude of the rising rate limit may equal the magnitude of the falling rate limit. Alternatively or additionally, while the rising and falling rate limits may respectively comprise positive and negative values, such is not required. For example, when the falling rate limit is set to a positive value, Equation (4) may be modified according to:

$$\Delta_a = -\min(\Delta_{r-}, P_{filt} - P_{inst}) \quad (5)$$

Similar modifications to Equation (3) may be made when the rising rate limit is set to a negative value.

Adjustment processor 130 may further include a modifier processor 134 configured to compute one or more modifiers based on one or more of the heuristic properties, and further configured to determine the rate limit as a function of the modifier(s) and an initial rate limit $\Delta_{init}$, e.g., as provided by rate processor 124. Accordingly, modifier processor 134 includes a calculator 136 and a modifier applicator 138. Calculator 136 computes one or more modifiers based on the one or more heuristic properties of the physiological waveform provided by the spectral transform. In some embodiments, the modifier(s) represent a reliability of the initial rate limit $\Delta_{init}$. Modifier applicator 138 subsequently applies the computed modifier(s) to the initial rate limit $\Delta_{init}$, e.g., by summing and/or multiplying the initial rate limit $\Delta_{init}$ by the computed modifier(s), to determine the rate limit $\Delta_r$ used by function processor 132. It will be appreciated that the modifier(s) may be applied to any initial rate limit $\Delta_{init}$, including the rising rate limit, the falling rate limit, or both, and that when function processor 132 uses different processing paths based on the comparison between $P_{inst}$ and $P_{filt}$, the modifiers are applied to the rate limits of one or more of the processing paths as needed/desired.

In one exemplary embodiment, calculator 136 computes a spectral modifier $\alpha_1$ based on heuristic properties of the physiological waveform comprising spectral characteristics of the instantaneous estimate of the heart rate. The spectral modifier quantifies the reliability (or confidence) that the spectral transformer 110 associated the instantaneous estimate with the correct spectral peak. Broadly, when there is a large difference in magnitude between the spectral peak having the largest magnitude and the spectral peak having the next largest magnitude, there is a high degree of confidence that the largest spectral peak corresponds to the instantaneous heart rate of interest. More particularly, the spectral transformer 110 may provide the spectral characteristics for some number of the spectral peaks of the spectrally transformed waveform, e.g., the magnitude(s) of two or more spectral peaks. For example, the spectral transformer may provide the magnitude of the largest spectral peak $SPM_1$ and the magnitude of the second largest spectral peak $SPM_2$ to the calculator 136. Based on the provided spectral magnitudes, calculator 136 calculates the spectral modifier. For example, calculator 136 may compute the spectral modifier according to:

$$\alpha_1 = 1 - \frac{SPM_2}{SPM_1}. \quad (6)$$

Subsequently, modifier applicator 138 applies the spectral modifier according to:

$$\Delta_r = \alpha_1 \Delta_{init} \quad (7)$$

It will be appreciated that applicator 138 may apply the spectral modifier to the initial rate limit $\Delta_{init}$ using linear means, e.g., multiplication, addition, subtraction, and/or division, or using non-linear means, e.g., norm, RMS, min, or max functions. It should be noted that if the magnitude of the largest peak ($SPM_1$) and the magnitude of the $2^{nd}$ largest peak ($SPM_2$) are identical, then $\alpha_1 = 0$, such that the rate limit $\Delta_r$ is zero. With the rate limit at zero, the reported physiological metric $\hat{P}_{filt}$ (which in this specific case is the reported heart rate) may not change.

In another exemplary embodiment, calculator 136 computes a boundary modifier $\alpha^2$ as a function of boundary values bounding the heart rate based on the comparison between the instantaneous estimate and the current filtered estimate. The boundary modifier also quantifies the reliability (or confidence) that the spectral transformer 110 associated the instantaneous estimate of the heart rate with the correct spectral peak based on the difference between the current filtered estimate and the instantaneous estimate. When there is a large difference between the instantaneous and current filtered estimates, there is a low degree of confidence that the instantaneous estimate is correct. More particularly, when the instantaneous estimate is greater than or equal to the current filtered estimate, the calculator 136 may compute the boundary modifier according to:

$$\alpha_2 = \frac{P_{max} - P_{inst}}{P_{max} - P_{filt}}, \qquad (8)$$

where $P_{max}$ represents an upper boundary for the heart rate. For example, $P^{max}$ may be set equal to 225 BPM. When the instantaneous estimate is less than the current filtered estimate, the calculator 136 may compute the boundary modifier according to:

$$\alpha_2 = \frac{P_{inst} - P_{min}}{P_{filt} - P_{min}}, \qquad (9)$$

where $P_{min}$ represents a lower boundary for the heart rate. For example, $P_{min}$ may be set equal to 40 BPM. Subsequently, modifier applicator 138 applies the boundary modifier according to:

$$\Delta_r = \alpha_2 \Delta_{init} \qquad (10)$$

It will be appreciated that applicator 138 may apply the boundary modifier to the initial rate limit $\Delta_{init}$ using linear means, e.g., multiplication, addition, subtraction, and/or division, or using non-linear means, e.g., norm, RMS, min, or max functions. It will also be appreciated that the upper and lower heart rate boundaries are based on empirical evidence, which indicates that most people, whether at rest or exercising, have a heart rate between 40 and 225 BPM.

In still another embodiment, calculator 136 may compute the spectral and boundary modifiers, as previously described. Subsequently, applicator 138 applies the spectral and boundary modifiers according to:

$$\Delta_r = \alpha_1 \alpha_2 \Delta_{init} \qquad (11)$$

It will be appreciated that applicator 138 may apply the spectral and boundary modifiers to the initial rate limit $\Delta_{init}$ using linear means, e.g., multiplication, addition, subtraction, and/or division, or using non-linear means, e.g., norm, RMS, min, or max functions. It will further be appreciated that other modifier(s) determined based on one or more heuristic properties of the physiological waveform may be additionally or alternatively applied to the initial rate limit $\Delta_{init}$ to determine $\Delta_r$.

Embodiments disclosed heretofore filter an estimate of the heart rate derived from a spectral transformation of the physiological waveform output by the sensor(s) 20. While such filtering improves the accuracy of the output heart rate, it will be appreciated that the accuracy may further be improved through the use of noise reduction techniques applied to the physiological waveform and/or to the instantaneous estimate before applying the filtering technique. For example, processor 100 may include an optional noise filter 140 (FIG. 4) configured to filter the physiological waveform output by the sensor(s) 20 to generate a noise-reduced waveform, e.g., a waveform free of breathing noise. In this example, spectral transformer 110 determines the instantaneous estimate and/or other spectral information used during the filtering process based on the noise-reduced waveform. In so doing, the processor 100 reduces the noise present in the instantaneous estimate and/or the revised filtered estimate. Alternatively or additionally, system 12 may include an optional inertial sensor 50 (FIG. 2), e.g., a motion sensor, configured to receive an inertial waveform representative of external energy, e.g., external motion. The motion sensor 50 may comprise one or more of any number of types of sensors, including but not limited to an accelerometer, an optical emitter/detector pair, an optical detector, a CCD camera, a piezoelectric sensor, a thermal sensor, or any type of sensor capable of capturing motion information. Exemplary optical emitters comprise one or more light emitting diodes, laser diodes, organic light-emitting diodes, miniature light emitters, electromagnetic emitters, etc. It will be appreciated that the sensors disclosed herein are not limited to optical wavelengths of the electromagnetic spectrum. In some embodiments, emitters and/or detectors configured for shorter or longer wavelengths may be used to accommodate shorter or longer wavelengths in the electromagnetic spectrum. The optical detector may comprise a photodetector, an electromagnetic detector, a photodiode, etc. In the filtering embodiment, spectral transformer 110 determines the instantaneous estimate and/or other spectral information used during the filtering process based on the inertial spectrum determined for the inertial waveform and the physiological spectrum determined for the physiological waveform. In so doing, the processor 100 reduces noise attributable to external energy/motion, e.g., energy due to a poor fit of the ear bud, shadows, etc., to reduce the noise present in the instantaneous estimate and/or the revised filtered estimate. For example, the spectral transformer may subtract the physiological and inertial spectrums to determine a reduced noise spectrum, and then may identify the frequency associated with the spectral peak having the largest magnitude as the instantaneous estimate of the heart rate. In still another embodiment, noise filter 140 may receive the inertial waveform and filter the physiological waveform based on the inertial waveform to generate the noise reduced waveform, where the spectral transformer 110 determines the instantaneous estimate and/or other spectral information based on the noise-reduced waveform.

Figure 6:
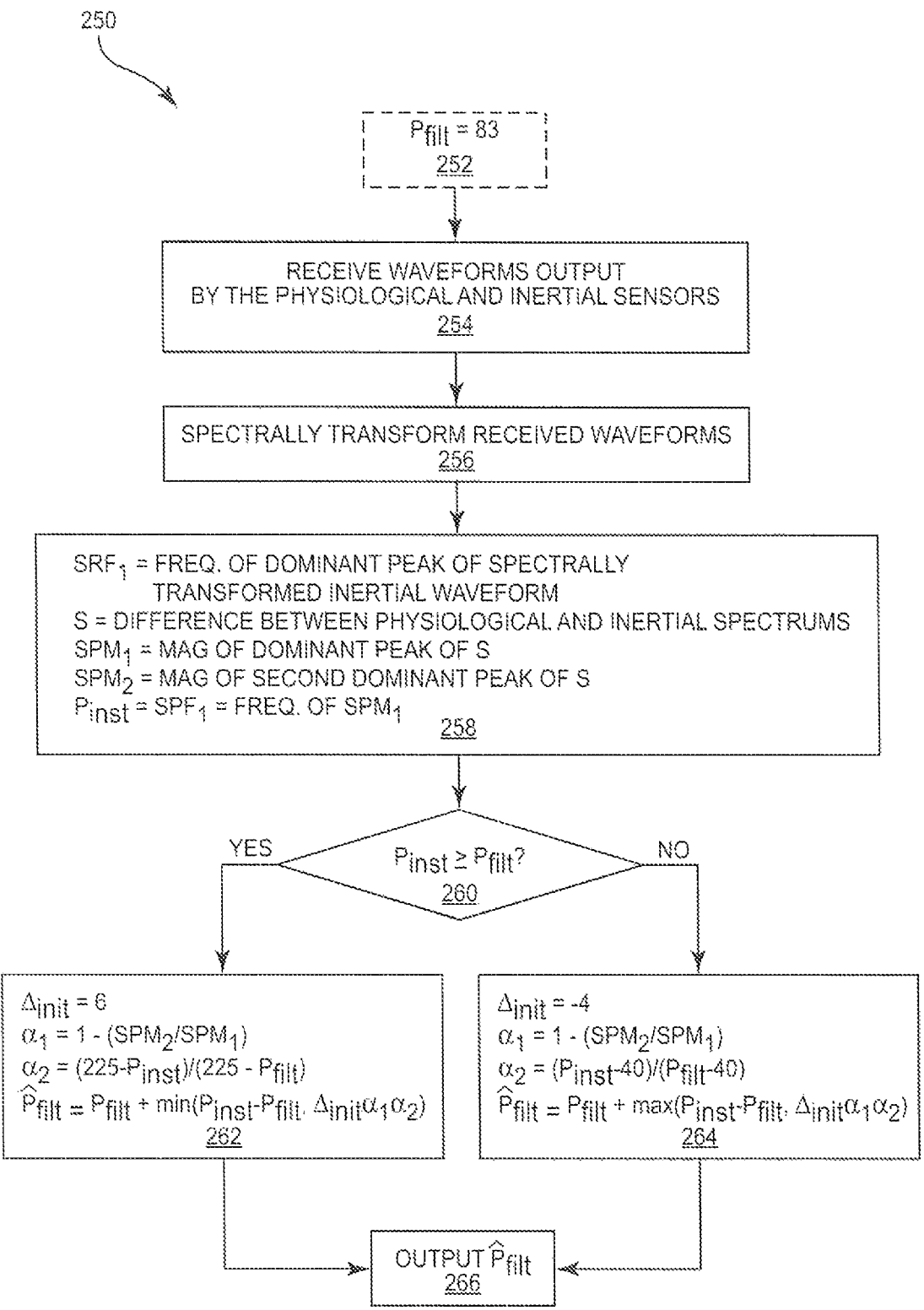
FIG. 6 shows another exemplary process for determining physiological information from data provided by a physiological sensor.

FIG. 6 shows one exemplary method 250 for the embodiment where the spectral and boundary modifiers are used to compute the rate limit used to determine $\hat{P}_{filt}$, and where the inertial waveform provided by an inertial sensor 50 is used to reduce noise as described herein. In this exemplary embodiment, $P_{filt}$ optionally comprises a current filtered heart rate initially set equal to 83 BPM (block 252). Spectral transformer 110 spectrally transforms the physiological and inertial waveforms respectively received from the physiological and inertial sensors (blocks 254, 256). The spectral transformer 110 subsequently identifies the frequency of the dominant peak of the spectrally transformed inertial waveform ($SRF_1$), computes the difference between the physiological and inertial spectrums (S), identifies the magnitudes of the dominant and second dominant peaks of S ($SPM_1$ and $SPM_2$, respectively), sets $P_{inst}$ equal to the frequency of the dominant peak ($SPF_1$) (block 258), and provides at least $P_{inst}$ to the filter 120. After comparing to $P_{filt}$ to $P_{inst}$ (block 260), filter 120 performs a filtering operation based on the comparison. For example, filter 120 performs the operations of block 262 when $P_{inst} \geq P_{filt}$, and performs the operations of block 264 when $P_{inst} < P_{filt}$. Subsequently, the processor outputs $P_{filt}$ (block 266).

The embodiments disclosed herein improve the accuracy of heart rates determined based on physiological waveforms provided by physiological sensors, particularly noise sensitive sensors, e.g., PPG sensors. In particular, the embodiments disclosed herein reduce the impact of noise sources not previously addressed by past systems, e.g., motion noise due to a user's jaw movement and/or breathing, shadow/sunlight flicker due to a user's movement into and out of shaded areas, light noise due to ambient light being detected by the photodetector, etc.

While the present invention is described in terms of PPG sensors, it will be appreciated that sensors 20 may comprise any sensor able to generate a physiological waveform, e.g., an electroencephalogram (EEG) waveform, and electrocardiogram (ECG) waveform, a radio frequency (RF) waveform, an electro-optical physiological waveform, a thermoelectric waveform, and electro-photoacoustic waveform including a photoacoustic waveform, an electro-mechanical physiological waveform, and/or an electro-nuclear physiological waveform.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A physiological processor disposed in a device secured to a body of a user, the physiological processor configured to process a time domain photoplethysmography waveform provided by a photoplethysmography sensor disposed in the device and in contact with skin of the user, the processor comprising:
   a spectral transformer configured to:
      convert the photoplethysmography waveform from the time domain to a frequency domain to generate a spectrum;
      identify a first spectral peak having a largest magnitude in the spectrum and a second spectral peak having a next largest magnitude in the spectrum; and
      determine, responsive to the spectrum, an instantaneous estimate of a heart rate; and
   a filter operatively connected to the spectral transformer and configured to:
      compare the instantaneous estimate to a current filtered estimate of the heart rate;
      determine of a rising rate limit or a falling rate limit depending respectively on whether the instantaneous estimate is larger or smaller than the current filtered estimate, wherein the rising rate limit or falling rate limit is determined relative to the current filtered estimate as a function of the first spectral peak and the second spectral peak;
      compute a revised filtered estimate of the heart rate as:
         a function of the rising rate limit when the instantaneous estimate is greater than or equal to the current filtered estimate;
         a function of the falling rate limit when the instantaneous estimate is less than the current filtered estimate; and
      output, to an output interface, the revised filtered estimate of the heart rate.

2. The physiological processor of claim 1 wherein the physiological processor is further configured to process information provided by the photoplethysmography sensor to determine at least one additional dynamically changing vital sign different from the heart rate.

3. The physiological processor of claim 1 wherein the current filtered estimate subtracted from the instantaneous estimate comprises a difference, and wherein the filter computes the revised filtered estimate of the heart rate by:
   when the instantaneous estimate is greater than or equal to the current filtered estimate, computing the revised filtered estimate of the heart rate as a sum of the current filtered estimate and a minimum of the rising rate limit and the difference; and
   when the instantaneous estimate is less than the current filtered estimate, computing the revised filtered estimate of the heart rate as a sum of the current filtered estimate and a maximum of a falling rate limit and the difference.

4. The physiological processor of claim 1 wherein when the instantaneous estimate is greater than or equal to the current filtered estimate, the filter computes the revised filtered estimate of the heart rate by:
   adding the current filtered estimate to the falling rate limit to compute a first value;
   adding the current filtered estimate to the rising rate limit to compute a second value;
   determining a minimum of the second value and the instantaneous estimate to compute a third value; and
   computing the revised filtered estimate of the heart rate as a maximum of the first value and the third value.

5. The physiological processor of claim 1 wherein when the instantaneous estimate is less than the current filtered estimate, the filter computes the revised filtered estimate of the heart rate by:
   adding the current filtered estimate to the rising rate limit to compute a first value;
   adding the current filtered estimate to the falling rate limit to compute a second value;
   determining a maximum of the second value and the instantaneous estimate to compute a third value; and
   computing the revised filtered estimate of the heart rate as a minimum of the first value and the third value.

6. The physiological processor of claim 1 wherein the rising rate limit and the falling rate limit have different magnitudes.

7. A method of processing data provided by a physiological sensor disposed in a device secured to a body of a user such that the physiological sensor is in contact with skin of the user, the method comprising:
   receiving a time domain physiological waveform from the physiological sensor;
   converting, using a spectral transformer disposed in the device and operatively connected to the physiological sensor, the received physiological waveform from the time domain to a frequency domain to generate a physiological spectrum;
   identifying a first spectral peak having a largest magnitude in the spectrum and a second spectral peak having a next largest magnitude in the spectrum;
   determining, using the physiological spectrum, an instantaneous estimate of a physiological metric;
   comparing, using a filter disposed in the device and operatively connected to the spectral transformer, the instantaneous estimate to a current filtered estimate of the physiological metric;
   determining, using the filter, a rising rate limit or a falling rate limit depending respectively on whether the instantaneous estimate is larger or smaller than the current filtered estimate, wherein the rising rate limit or falling rate limit is determined relative to the current filtered estimate as a function of the first spectral peak and the second spectral peak;

computing, using the filter, a revised filtered estimate of
the physiological metric as:
a function of the rising rate limit when the instantaneous estimate is greater than or equal to the current filtered estimate;
a function of the falling rate limit when the instantaneous estimate is less than the current filtered estimate; and
outputting the revised filtered estimate to an output interface.

8. The method of claim 7 wherein outputting the revised filter estimate comprises outputting the revised filter estimate to at least one of a user interface, a transceiver, a database, a processor, and a processing function.

9. The method of claim 7 wherein the physiological metric comprises a heart rate.

10. The method of claim 7 wherein receiving the physiological waveform comprises receiving the physiological waveform from a photoplethysmography (PPG) sensor.

11. The method of claim 7 wherein the current filtered estimate subtracted from the instantaneous estimate comprises a difference, and wherein computing the revised filtered estimate of the physiological metric comprises:
when the instantaneous estimate is greater than or equal to the current filtered estimate, computing the revised filtered estimate of the physiological metric as a sum of the current filtered estimate and a minimum of the rising rate limit and the difference; and
when the instantaneous estimate is less than the current filtered estimate, computing the revised filtered estimate of the physiological metric as a sum of the current filtered estimate and a maximum of the falling rate limit and the difference.

12. The method of claim 7 wherein when the instantaneous estimate is greater than or equal to the current filtered estimate, the computing the revised filtered estimate of the physiological metric comprises:
adding the current filtered estimate to the falling rate limit to compute a first value;
adding the current filtered estimate to the rising rate limit to compute a second value;
determining a minimum of the second value and the instantaneous estimate to compute a third value; and
computing the revised filtered estimate of the physiological metric as a maximum of the first value and the third value.

13. The method of claim 7 wherein when the instantaneous estimate is less than the current filtered estimate, the computing the revised filtered estimate of the physiological metric comprises:
adding the current filtered estimate to the rising rate limit to compute a first value;
adding the current filtered estimate to the falling rate limit to compute a second value;
determining a maximum of the second value and the instantaneous estimate to compute a third value; and
computing the revised filtered estimate of the physiological metric as a minimum of the first value and the third value.

14. The method of claim 7 wherein the rising rate limit and the falling rate limit have different magnitudes.

15. The method of claim 7 wherein the function of the first spectral peak and the second spectral peak comprises summing a magnitude of the first spectral peak with a magnitude of the second spectral peak.

16. The method of claim 7 wherein the function of the first spectral peak and the second spectral peak comprises multiplying a magnitude of the first spectral peak with a magnitude of the second spectral peak.

17. The method of claim 7 wherein determining the rising rate limit or the falling rate limit relative to the current filtered estimate as the function of the first spectral peak and the second spectral peak comprises determining the rising rate limit or the falling rate limit relative to the current filtered estimate as a function of the first spectral peak, the second spectral peak, and a predetermined initial rate limit.

18. The method of claim 17 further comprising computing a first modifier as a function of a boundary value associated with the physiological metric and one or more properties of the physiological waveform, and wherein determining the rising rate limit or the falling rate limit relative to the current filtered estimate as the function of the first spectral peak, the second spectral peak, and the predetermined initial rate limit comprises applying the first modifier to the predetermined initial rate limit.

19. The method of claim 17 further comprising computing a first modifier as a function of the first spectral peak and the second spectral peak, wherein determining the rising rate limit or the falling rate limit relative to the current filtered estimate as the function of the first spectral peak, the second spectral peak and the predetermined initial rate limit comprises applying the first modifier to the predetermined initial rate limit.

20. The method of claim 19 further comprising computing a second modifier as a function of a boundary value associated with the physiological metric and one or more properties of the physiological waveform, wherein determining the rising rate limit or the falling rate limit relative to the current filtered estimate as the function of the first spectral peak, the second spectral peak, and the predetermined initial rate limit comprises applying the first and second modifiers to the predetermined initial rate limit.

21. The method of claim 19 wherein computing the first modifier comprises computing the first modifier as a function of a ratio between the second spectral peak and the first spectral peak.

22. The method of claim 7 wherein the rising rate limit comprises a first rate limit for an increasing physiological metric and the falling rate limit comprises a second rate limit for a decreasing physiological metric, where a magnitude of the first rate limit relative to the current filtered estimate is different from a magnitude of the second rate limit relative to the current filtered estimate, the method further comprising selecting the first or second rate limit responsive to the comparison between the instantaneous estimate and the current filtered estimate.

23. A physiological processor disposed in a device secured to a body of a user, the physiological processor configured to process a time domain physiological waveform provided by a physiological sensor disposed in the device and in contact with skin of the user, the processor comprising:
a spectral transformer configured to:
convert the physiological waveform from the time domain to a frequency domain to generate a physiological spectrum;
identify a first spectral peak having a largest magnitude in the spectrum and a second spectral peak having a next largest magnitude in the spectrum; and
determine, using the physiological spectrum, an instantaneous estimate of a physiological metric; and a filter operatively connected to the spectral transformer and configured to:
  compare the instantaneous estimate to a current filtered estimate of the physiological metric;
  determine a rising rate limit or a falling rate limit depending respectively on whether the instantaneous estimate is larger or smaller than the current filtered estimate, wherein the rising rate limit or falling rate limit is determined relative to the current filtered estimate as a function of the first spectral peak and the second spectral peak;
  compute a revised filtered estimate of the physiological metric as:
    a function of the rising rate limit when the instantaneous estimate is greater than or equal to the current filtered estimate;
    a function of the falling rate limit when the instantaneous estimate is less than the current filtered estimate; and
  output, to an output interface, the revised filtered estimate of the physiological metric.

24. The physiological processor of claim 23 further comprising an output element configured to receive the revised filter estimate from the filter, said output element comprising at least one of a user interface, transceiver, a database, a processor, and a processing function.

25. The physiological processor of claim 23 wherein the physiological metric comprises a heart rate.

26. The physiological processor of claim 23 wherein the physiological sensor comprises a photoplethysmography (PPG) sensor.

27. The physiological processor of claim 23 wherein the current filtered estimate subtracted from the instantaneous estimate comprises a difference, and wherein the filter computes the revised filtered estimate of the physiological metric by:
  when the instantaneous estimate is greater than or equal to the current filtered estimate, computing the revised filtered estimate of the physiological metric as a sum of the current filtered estimate and a minimum of the rising rate limit and the difference; and
  when the instantaneous estimate is less than the current filtered estimate, computing the revised filtered estimate of the physiological metric as a sum of the current filtered estimate and a maximum of the falling rate limit and the difference.

28. The physiological processor of claim 23 wherein when the instantaneous estimate is greater than or equal to the current filtered estimate, the filter computes the revised filtered estimate of the physiological metric by:
  adding the current filtered estimate to the falling rate limit to compute a first value;
  adding the current filtered estimate to the rising rate limit to compute a second value;
  determining a minimum of the second value and the instantaneous estimate to compute a third value; and
  computing the revised filtered estimate of the physiological metric as a maximum of the first value and the third value.

29. The physiological processor of claim 23 wherein when the instantaneous estimate is less than the current filtered estimate, the filter computes the revised filtered estimate of the physiological metric by:
  adding the current filtered estimate to the rising rate limit to compute a first value;
  adding the current filtered estimate to the falling rate limit to compute a second value;
  determining a maximum of the second value and the instantaneous estimate to compute a third value; and
  computing the revised filtered estimate of the physiological metric as a minimum of the first value and the third value.

30. The physiological processor of claim 23 wherein the rising rate limit and the falling rate limit have different magnitudes.

31. The physiological processor of claim 23 wherein the function of the first spectral peak and the second spectral peak comprises a sum of a magnitude of the first spectral peak with a magnitude of the second spectral peak.

32. The physiological processor of claim 23 wherein the function of the first spectral peak and the second spectral peak comprises multiplying a magnitude of the first spectral peak with a magnitude of the second spectral peak.

33. The physiological processor of claim 24 wherein the filter is configured to determine the rising rate limit or the falling rate limit relative to the current filtered estimate by determining the rising rate limit or the falling rate limit relative to the current filtered estimate as a function of the first spectral peak, the second spectral peak, and a predetermined initial rate limit.

34. The physiological processor of claim 33 wherein the filter comprises: a calculator configured to compute a first modifier as a function of a boundary value associated with the physiological metric and one or more properties of the physiological waveform; and a modifier applicator configured to apply the first modifier to the predetermined initial rate limit to determine the rising rate limit or the falling rate limit relative to the current filtered estimate.

35. The physiological processor of claim 33 wherein the filter comprises: a calculator configured to compute a first modifier as a function of the first spectral peak and the second spectral peak; and a modifier applicator configured to apply the first modifier to the predetermined initial rate limit to determine the rising rate limit or the falling rate limit relative to the current filtered estimate.

36. The physiological processor of claim 35 wherein the calculator is further configured to compute a second modifier as a function of a boundary value associated with the physiological metric and one or more properties of the physiological waveform, and wherein the modifier applicator is configured to apply the first and second modifiers to the predetermined initial rate limit to determine the rising rate limit or the falling rate limit relative to the current filtered estimate.

37. The physiological processor of claim 35 wherein the calculator is configured to compute the first modifier as a function of a ratio between a second spectral peak of the one or more spectral peaks and the first spectral peak, said second spectral peak having a smaller amplitude than the first spectral peak and a larger amplitude than the remaining spectral peaks.

38. The physiological processor of claim 23 wherein the rising rate limit comprises a first rate limit for an increasing physiological metric and the falling rate limit comprises a second rate limit for a decreasing physiological metric, where a magnitude of the first rate limit relative to the current filtered estimate is different from a magnitude of the second rate limit relative to the current filtered estimate, and wherein the filter comprises a rate processor configured to select the first rate limit or the second rate limit responsive to the comparison between the instantaneous estimate and the current filtered estimate.

* * * * *